United States Patent [19]

Zinnen

[11] Patent Number: 4,956,522

[45] Date of Patent: Sep. 11, 1990

[54] ZEOLITIC PARA-ETHYLTOLUENE SEPARATION WITH TETRALIN HEAVY DESORBENT

[75] Inventor: Hermann A. Zinnen, Evanston, Ill.

[73] Assignee: UOP, Des Plaines, Ill.

[21] Appl. No.: 439,058

[22] Filed: Nov. 20, 1989

Related U.S. Application Data

[63] Continuation-in-part of Ser. No. 197,787, May 23, 1988, Pat. No. 4,886,930.

[51] Int. Cl.$^5$ ............................................. C07C 7/12
[52] U.S. Cl. ................................................... 585/828
[58] Field of Search ........................... 585/828, 820; 208/310.7

[56] References Cited

U.S. PATENT DOCUMENTS

| | | | |
|---|---|---|---|
| 2,985,589 | 5/1961 | Broughton | 210/34 |
| 3,040,777 | 6/1962 | Carson et al. | 137/525.15 |
| 3,422,848 | 1/1969 | Liebman et al. | 137/525.15 |
| 3,626,020 | 12/1971 | Neuzil | 260/674 SA |
| 3,663,638 | 5/1972 | Neuzil | 260/674 SA |
| 3,665,046 | 5/1972 | De Rosset | 260/674 SA |
| 3,668,266 | 6/1972 | Chen et al. | 260/674 SA |
| 3,686,342 | 8/1972 | Neuzil | 260/674 SA |
| 3,700,744 | 10/1972 | Berger et al. | 260/668 A |
| 3,706,812 | 12/1972 | De Rosset et al. | 260/674 SA |
| 3,737,974 | 5/1973 | Neuzil | 260/674 SA |
| 3,894,109 | 7/1975 | Rosback | 260/674 SA |
| 3,997,620 | 12/1976 | Neuzil | 260/674 SA |
| 4,014,949 | 3/1977 | Hedge | 260/674 SA |
| 4,051,192 | 9/1977 | Neuzil et al. | 260/674 SA |
| 4,100,217 | 7/1978 | Young | 260/671 R |
| 4,159,284 | 6/1979 | Seko et al. | 585/473 |
| 4,402,832 | 9/1983 | Gerhold | 210/659 |
| 4,423,279 | 12/1983 | Kulprathipanja | 585/828 |
| 4,478,721 | 10/1984 | Gerhold | 210/659 |
| 4,482,777 | 3/1977 | Hedge | 260/674 SA |
| 4,642,397 | 2/1987 | Zinnen et al. | 568/934 |

*Primary Examiner*—Glenn Caldarola
*Attorney, Agent, or Firm*—Thomas K. McBride; John F. Spears, Jr.; Jack H. Hall

[57] ABSTRACT

A chromatographic process able to separate para-ethyltoluene from feed mixtures of $C_8$ and/or $C_9$ aromatic hydrocarbons. In the process, the para-ethyltoluene-containing feed mixture is contacted with a Y zeolite adsorbent having potassium at exchangeable cationic sites. The para-ethyltoluene is selectively adsorbed onto the adsorbent. The non-adsorbed components of the feed are then removed from the adsorbent and the para-ethyltoluene recovered by desorption with tetralin or alkyl or dialkyl derivatives of tetralin or alkyl derivatives of naphthalene. The other $C_9$'s and the xylene isomers in the raffinate and p-ethyltoluene in the extract can be separated from the heavy desorbent by fractionation of the raffinate or extract and the desorbent recycled to the process.

6 Claims, 2 Drawing Sheets

४,९५६,५२२

ZEOLITIC PARA-ETHYLTOLUENE SEPARATION WITH TETRALIN HEAVY DESORBENT

CROSS REFERENCE TO RELATED APPLICATIONS

This application is a continuation-in-part of my prior copending application, Ser. No. 197,787 filed on May 23, 1988, now U.S. Pat. No. 4,886,930 all of the teachings of which are incorporated herein by reference thereto.

FIELD OF THE INVENTION

The field of art to which the claimed invention pertains is hydrocarbon separation. More specifically, the invention relates to a process for separating para-ethyltoluene from a feed mixture comprising one or more xylene isomers and/or other $C_9$ aromatics, which process employs a zeolite adsorbent and particular desorbents.

BACKGROUND OF THE INVENTION

Highly pure para-methyl styrene has recently become significant as a monomer or comonomer for making specialty vinyltoluene polymers and copolymers having improved high temperature properties, e.g., Vicat softening point and density, compared to polystyrene. Para-methyl styrene can be produced commercially by catalytic dehydrogenation of para-ethyltoluene.

In numerous processes described in the patent literature, for example U.S. Pat. Nos. 3,626,020 to Neuzil, 3,663,638 to Neuzil, 3,665,046 to deRosset, 3,668,266 to Chen et al., 3,686,342 to Neuzil et al., 3,700,744 to Berger et al., 3,734,974 to Neuzil, 3,894,109 to Rosback, 3,997,620 to Neuzil, 4,482,777 to Neuzil, and 4,014,949 to Hedge, particular zeolitic adsorbents are used to separate the para isomer of dialkyl substituted monocyclic aromatics from the other isomers, particularly paraxylene from other xylene isomers. Other patents, e.g., U.S. Pat. Nos. 4,051,192 to Neuzil et al and 4,423,279 to Kulprathipanja specifically disclose adsorptive separations selective for the para-isomer of ethyltoluene with potassium or barium-exchanged X zeolites or a pyrolyzed zeolitic adsorben, respectively. Many of the above patents use benzene, toluene, or p-diethylbenzene as the desorbent. P-diethylbenzene (p-DEB) has become the commercial standard for para-xylene separation. However, p-DEB suffers in the process for separating feed mixtures containing $C_9$ aromatic because the boiling point of p-DEB is too close to the boiling point of $C_9$ aromatics in the feed. Because the $C_9$ aromatics are difficult to separate from p-DEB by simple fractionation, the $C_9$ aromatics would gradually build up in the desorbent, which must be recycled for economic reasons. U.S. Pat. No. 3,686,342, supra, mentions tetralin as a possible heavy desorbent for the paraxylene separation process, but does not address the problem that the preferred desorbents may have in separating feeds containing $C_9$ aromatics. Therefore, a higher boiling point material that meets the selectivity requirements for desorbents and can be separated from $C_9$ aromatics is desirable.

It is also known that crystalline aluminosilicates or zeolites are used in adsorption separations of various mixtures in the form of agglomerates having high physical strength and attrition resistance. Methods for forming the crystalline powders into such agglomerates include the addition of an inorganic binder, generally a clay comprising a silicon dioxide and aluminum oxide, to the high purity zeolite powder in wet mixture. The blended clay zeolite mixture is extruded into cylindrical type pellets or formed into beads which are subsequently calcined in order to convert the clay to an amorphous binder of considerable mechanical strength. As binders, clays of the kaolin type, water permeable organic polymers or silica are generally used.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRosset U.S. Pat. No. 3,706,812) to commercial scale in flow rates from a few cc per hour to many thousands of gallons per hour.

The invention may also be practiced in a cocurrent, pulsed batch process, like that described in U.S. Pat. No. 4,159,284 or in a cocurrent pulsed continuous process, like that disclosed in Gerhold, U.S. Pat. Nos. 4,402,832 and 4,478,721.

The functions and properties of adsorbents and desorbents in the chromatographic separation of liquid components are well-known, but for reference thereto, Zinnen et al. U.S. Pat. No. 4,642,397 is incorporated herein.

I have discovered a process for employing a zeolite adsorbent for the separation of p-ethyltoluene from other $C_9$ and $C_8$ aromatic hydrocarbons and, particularly, a desorbent which is a substantial improvement in a process for separating p-ethyltoluene from feed mixtures containing other $C_9$ aromatic impurities, including isomers of p-ethyltoluene.

SUMMARY OF THE INVENTION

In brief summary, the invention is a chromatographic process for separating p-ethyltoluene from a feed mixture comprising p-ethyltoluene and at least one component selected from other $C_9$ aromatic hydrocarbons and xylene isomers (including ethylbenzene) comprising contacting said feed mixture with a Y-type zeolite exchanged with potassium ions at exchangeable cationic sites to effect the selective adsorption of said p-ethyltoluene and produce a raffinate comprising the other xylene isomers, including ethylbenzene, and $C_9$ aromatics. P-ethyltoluene is recovered by contacting the adsorbent with a desorbent comprising 1,2,3,4-tetrahydronaphthalene (tetralin) or lower alkyl ($C_{1-3}$) derivatives of tetralin or alkyl derivatives of naphthalenes. These desorbents are higher boiling (tetralin-b.p. 206° C. 1 methyl naphthalene-b.p. 245° C.) than p-ethyltoluene and the $C_9$ aromatics, making it possible to separate p-ethyltoluene and the other $C_9$ aromatics from the desorbent by simple fractionation so that the desorbent can be reused in the process without building up $C_9$ aromatics in the recycled desorbent.

Figure 1:
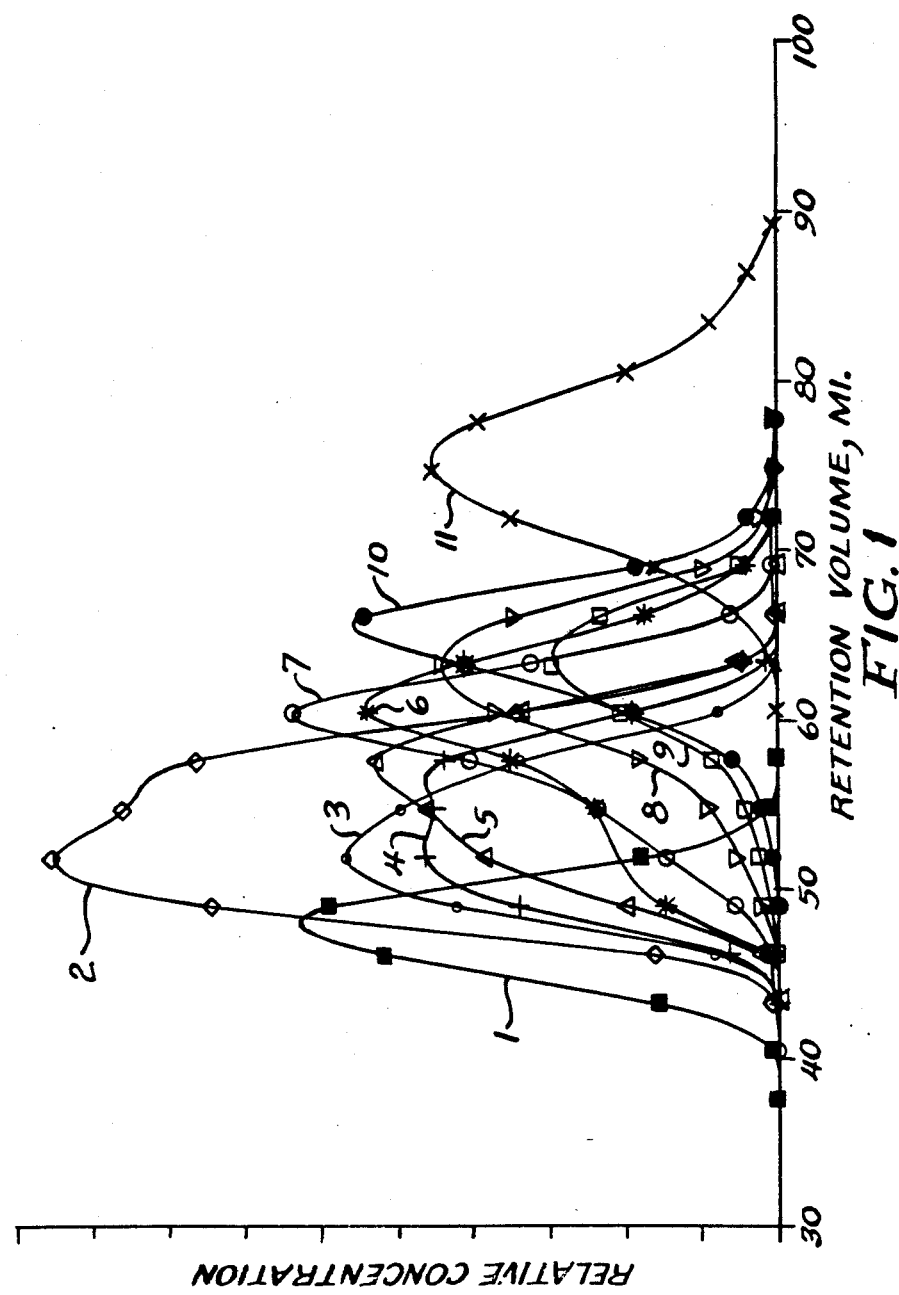
FIG. 1 is a chromatographic representation of the separation of p-ethyltoluene from a mixture of $C_8$ and $C_9$ aromatics with a K-exchanged Y zeolite and a desorbent comprising a 30/70 mixture of tetralin and n-heptane.

In the figures, numerals are used to indicate the component lines in the graph of relative concentrations vs. retention volume (ml.) as follows: the tracer 1; mesitylene 2; m-xylene 3; n-propylbenzene 4; o-xylene 5; 1,2,3-trimethylbenzene 6; ethylbenzene 7; 1,2,4-trimethylbenzene 8; cumene 9; p-xylene 10 and p-ethyltoluene 11.

DETAILED DESCRIPTION OF THE INVENTION

Adsorbents to be used in the process of this invention comprise specific crystalline aluminosilicates or molecular sieves, namely Y zeolites. The zeolites have known cage structures in which the alumina and silica tetrahedra are intimately connected in an open three-dimensional network to form cage-like structures with window-like pores. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves", although widely used, is not strictly suitable since the separation of specific aromatic isomers is apparently dependent on differences in electrochemical attraction of the different isomers and the adsorbent rather than on pure physical size differences in the isomer molecules.

The type Y structured zeolite, in the hydrated or partially hydrated form, can be represented in terms of moles of oxides as in Formula 1 below:

Formula 1

$(0.9 \pm 0.2)m_{2/n}O:Al_2O_3:wSiO_2:yH_2O$ where "M" is a cation having a valence of not more than 3 which balances the electrovalence of the tetrahedra and is generally referred to as an exchangeable cationic site, "n" represents the valence of the cation, "w" is a value greater than about 3 up to about 6 and "y", which represents the moles of water, is a value up to about 9 depending upon the identity of "M" and the degree of hydration of the crystal. The $SiO_2/Al_2O_3$ mole ratio for type Y structured zeolites can thus be from about 3 to about 6. As initially prepared, the cation "M" is usually predominately sodium. The type Y zeolite containing predominately sodium cations at the exchangeable cationic sites is, therefore, referred to as a sodium-exchanged type-Y, or NaY, zeolite. Depending upon the purity of the reactants used to make the zeolite, other cations mentioned above may be present, however, as impurities.

The zeolites useful in the invention include Y zeolites in which the exchange sites are occupied by potassium ions.

Typically, adsorbents used in separative processes contain the crystalline material dispersed in an amorphous, inorganic matrix or binder, having channels and cavities therein which enable liquid access to the crystalline material. Silica, alumina, clay or mixtures thereof are typical of such inorganic matrix materials. The binder aids in forming or agglomerating the crystalline particles which otherwise would comprise a fine powder. The adsorbent may thus be in the form of particles such as extrudates, aggregates, tablets, macrospheres or granules having a desired particle range, preferably from about 16 to about 60 mesh (Standard U.S. Mesh) (1.9 mm to 250 micron).

Feed mixtures which can be utilized in the process of this invention will comprise para-ethyltoluene, at least one other $C_9$ aromatic hydrocarbon and may also contain one or more $C_8$ aromatic hydrocarbon. Mixtures containing substantial quantities of xylenes and other $C_9$ aromatic hydrocarbons generally are produced by reforming and isomerization processes, processes which are well known to the refining and petrochemical arts. Many of the $C_9$ aromatics have boiling points in the range of 160°–170° C. and cannot be easily removed by distillation from the standard desorbent, p-diethylbenzene. I have discovered certain desorbents which can be easily separated from the $C_9$ aromatics by fractionation.

Alkylation processes can provide feed mixtures for the process of the invention. In a well-known alkylation process, toluene is contacted with an aluminum chloride catalyst in liquid phase to produce an effluent containing m-, p- and o-ethyltoluene. While more recently developed catalysts, such as ZSM-23, disclosed in U.S. Pat. No. 4,100,217, are more selective for the para-isomer and can reportedly effect up to 97% pure para-isomer, in all commercially practiced processes it is desirable to increase the purity of the para-isomer, if it can be done economically enough.

Reforming processes can also provide feed mixtures for the process of this invention. In reforming processes, a naphtha feed is contacted with a platinum-halogen-containing catalyst at severities selected to produce an effluent containing $C_8$ and $C_9$ aromatic isomers. Generally, the reformate is then fractionated to concentrate the $C_8$ aromatic isomers, but $C_9$ aromatics will also be present as impurities. Feed mixtures for the process of this invention may also be obtained from isomerization and transalkylation processes. Xylene mixtures which are deficient in one or more isomers can be isomerized, at isomerization conditions, to produce an effluent containing $C_8$ aromatic isomers, e.g., enriched in p-xylene, as well as $C_8$ nonaromatics and $C_9$ aromatics. The $C_9$ aromatic content of isomerized xylene isomers can be as much as 1–2% depending on isomerization conditions. Likewise, transalkylation of mixtures of $C_7$ and $C_9$ aromatics produces xylene isomers. Previously, $C_9$ aromatics were removed from $C_8$ aromatics by distillation before conventional adsorptive xylene separation methods were employed. Thus, the invention may be used to remove p-ethyltoluene from process streams containing small amounts as impurities or substantial quantities in admixture with other $C_9$ aromatic hydrocarbons, including isomers of p-ethyltoluene.

To separate the para-ethyltoluene from a feed mixture containing para-ethyltoluene and xylenes or other $C_8$ or $C_9$ aromatic hydrocarbons, the mixture is contacted with the adsorbent at adsorption conditions and the para-ethyltoluene is more selectively adsorbed and retained by the adsorbent while the other components are relatively unadsorbed and are removed from the interstitial void spaces between the particles of adsorbent and from the surface of the adsorbent. The adsorbent containing the more selectively adsorbed para-ethyltoluene is referred to as a "rich" adsorbent—rich in the more selectively adsorbed para-ethyltoluene. The para-ethyltoluene is then recovered from the rich adsorbent by contacting the rich adsorbent with a desorbent material at desorption conditions.

In this process, which employs zeolitic adsorbents and which is generally operated continuously at substantially constant pressures and temperatures to ensure liquid phase, the desorbent material relied upon must be judiciously selected to satisfy several criteria. First, the desorbent material should displace an extract component from the adsorbent with reasonable mass flow rates without itself being so strongly adsorbed as to unduly prevent the extract component from displacing the desorbent material in a following adsorption cycle. Secondly, the desorbent material must be compatible with the particular adsorbent and the particular feed mixture. More specifically, they must not reduce or destroy the critical selectivity of the adsorbent for an extract component with respect to the raffinate component or react chemically with the feed components. Desorbent materials should additionally be easily separable from the feed mixture that is passed into the process. Both the raffinate components and the extract components are typically removed from the adsorbent in admixture with desorbent material and without a method of separating at least a portion of desorbent material, the purity of the extract product and the raffinate product would not be very high nor would the desorbent material be available for reuse in the process. It is, therefore, contemplated that any desorbent material used in this process will have a substantially different average boiling point than that of the feed mixture or any of its components, i.e., more than about 5° C. difference, to allow separation of at least a portion of the desorbent material from feed components in the extract and raffinate streams by simple fractional distillation, thereby permitting reuse of desorbent material in the process.

Finally, desorbent materials should be readily available and reasonable in cost. However, a suitable desorbent or desorbents for a particular separation with specific adsorbent are not always predictable. In the preferred isothermal, isobaric, liquid-phase operation of the process of this invention, when the feed material to the separation process contains more than about 0.1% $C_9$ aromatics, I have found that a desorbent material comprising tetralin or lower alkyl or dialkyl derivatives of tetralin or alkyl derivatives of naphthalene will desorb the extract from the adsorbent and can be separated from $C_9$'s by distillation.

Suitable alkyl-substituted derivatives of tetralin include methyl tetralin, ethyl tetralin, propyl tetralin, isopropyltetralin, etc. Suitalbe dialkyl-substituted derivatives of tetralin include methyl ethyl tetralin, dimethyl tetralin, diethyltetralin, etc. Mixtures of tetralin with one or more of these derivatives, as well as mixtures of these derivatives also may be used with good results. In addition to tetralin, methyl tetralin and 2,6-dimethyl tetralin are preferred as desorbents in this process. All position isomers and mixtures are intended to be included when any tetralin derivative is referred to herein.

Suitable alkyl-substituted derivatives of naphthalene include 1-methyl naphthalene, 2-methyl naphthalene, 1-ethyl naphthalene, 2-ethyl naphthalene, propyl naphthalene, isomers, etc. Suitable dialkyl substituted derivatives of naphthalene include methyl ethyl naphthalene, dimethyl naphthalene, diethyl naphthalene, etc. Mixtures of tetralin or alkyl-substituted tetralin with one or more of these derivatives, as well as mixtures of these derivatives also may be used with good results. Preferred naphthalene derivatives are 1-methyl naphthalene and 2,6-dimethyl naphthalene. All position isomers and mixtures are intended to be included when any naphthalene derivative is referred to herein.

Adsorption conditions will include a temperature range of from about 20° to about 250° C. with about 60° to about 200° C. being more preferred and a pressure just sufficient to maintain liquid phase, which may be from about atmospheric to 600 psig. Desorption conditions will include the same range of temperatures and pressure as used for adsorption conditions.

A dynamic testing apparatus is employed to test various adsorbents and desorbent material with a particular feed mixture to measure the adsorbent characteristics of adsorptive capacity and exchange rate. The apparatus consists of a helical adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative equipment, such as refractometers, polarimeters, chromatographs, etc., can be attached to the outlet line of the chamber and used to analyze, "on-stream", the effluent stream leaving the adsorbent chamber.

A pulse test, performed using this apparatus and the following general procedure, is used to determine data, e.g., selectivities, for various adsorbent systems. The adsorbent is filled to equilibrium with a particular desorbent by passing the desorbent material through the adsorbent chamber. At a convenient time, a pulse of feed containing known concentrations of a tracer and of a particular extract component or of a raffinate component, or both, all diluted in desorbent material is injected for a duration of several minutes. Desorbent flow is resumed, and the tracer and the extract and raffinate components are eluted as in a liquid-solid chromatographic operation. The effluent can be analyzed by on-stream chromatographic equipment and traces of the envelopes of corresponding component peaks developed. Alternatively, effluent samples can be collected periodically and later analyzed separately by gas chromatography.

From information derived from the test, adsorbent performance can be rated in terms of void volume, retention volume for an extract or a raffinate component, and the rate of desorption of an extract component from the adsorbent and selectivity. Void volume is the non-selective volume of the adsorbent, which is expressed by the amount of desorbent pumped during the interval from initial flow to the center of the peak envelope of the tracer. The net retention volume (net) of an extract or a raffinate component may be characterized by the distance between the center of the peak envelope (gross retention volume) of the extract or raffinate component and the center of the peak envelope (void volume) of the tracer component or some other known reference point. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent material pumped during this time interval. Selectivity, $\beta$, is determined by the ratio of the net retention volumes of the more strongly adsorbed component to each of the other components.

The following non-limiting examples are presented to illustrate the process of the present invention and are not intended to unduly restrict the scope of the claims attached hereto.

EXAMPLE I

In this experiment, a pulse test, using the apparatus as described above, was performed to evaluate the ability of the present invention to separate para-ethyltoluene (b.p. 162° C.) from the xylene isomers and ethylbenzene (b.p.'s from 136°-145° C.) and from other $C_9$ aromatics. The adsorbent used was a Y faujasite exchanged with potassium, dried to yield a loss upon ignition (LOI) of 1.26% at 900° C. combined with 15 wt. % of an amorphous clay binder.

For each pulse test, the column was maintained at a temperature of 150° C. and at a pressure of 165 psig so as to maintain liquid-phase operations. Gas chromatographic analysis equipment was attached to the column effluent stream in order to determine the composition of the effluent material at given time intervals. The feed mixture employed for each test was 5 cc of a mixture containing 0.45 cc each of the xylene isomers and ethylbenzene and each of the following $C_9$ aromatics: cumene, n-propylbenzene, p-ethyltoluene, mesitylene, 1,2,4-trimethylbenzene and 1,2,3-trimethylbenzene. Normal nonane (0.45 cc) was used as a tracer and 4.95 cc desorbent material was added to the feed. The desorbent material comprised 30 vol. % tetralin with the remainder being n-$C_7$ paraffin. The operations taking place for the test were as follows: The desorbent material was run continuously at a rate of about 1.44 cc per minute. At some convenient time interval, the desorbent was stopped and the feed mixture was run for a 3.47 minute interval. The desorbent stream was then resumed and continued to pass into the adsorbent column until all of the feed aromatics had been eluted from the column as determined by chromatographic analysis of the effluent material leaving the adsorption column.

The results of the tests shown in Table 1 and the chromatographic tracing of FIG. 1 illustrate the invention. The table lists the gross retention volume (GRV) and net retention volume (NRV) for each component of the feed and the selectivity, $\beta$, for each component with respect to the reference, p-ethyltoluene.

TABLE 1

| Component | Gross Retention Volume (ml) | Net Retention Volume (ml) | Selectivity $\beta$ | Boiling Point |
| --- | --- | --- | --- | --- |
| n-Nonane | 47.7 | 0.0 | Tracer | |
| Ethylbenzene | 59.8 | 12.1 | 2.27 | 136 |
| p-Xylene | 65.0 | 17.3 | 1.59 | 138 |
| Cumene | 63.3 | 15.7 | 1.75 | 153 |
| o-Xylene | 55.6 | 7.9 | 3.48 | 144 |
| n-Propylbenzene | 53.9 | 6.3 | 4.36 | 159 |

TABLE 1-continued

| Component | Gross Retention Volume (ml) | Net Retention Volume (ml) | Selectivity $\beta$ | Boiling Point |
| --- | --- | --- | --- | --- |
| p-Ethyltoluene | 75.2 | 27.5 | 1.00 (Ref.) | 162 |
| Mesitylene | 53.6 | 5.9 | 4.66 | 163 |
| 1,2,4-Trimethylbenzene | 62.9 | 15.3 | 1.80 | 168 |
| 1,2,3-Trimethylbenzene | 60.3 | 12.6 | 2.18 | 175 |
| m-Xylene | 53.0 | 5.3 | 5.19 | 139 |

EXAMPLE II

Figure 2:
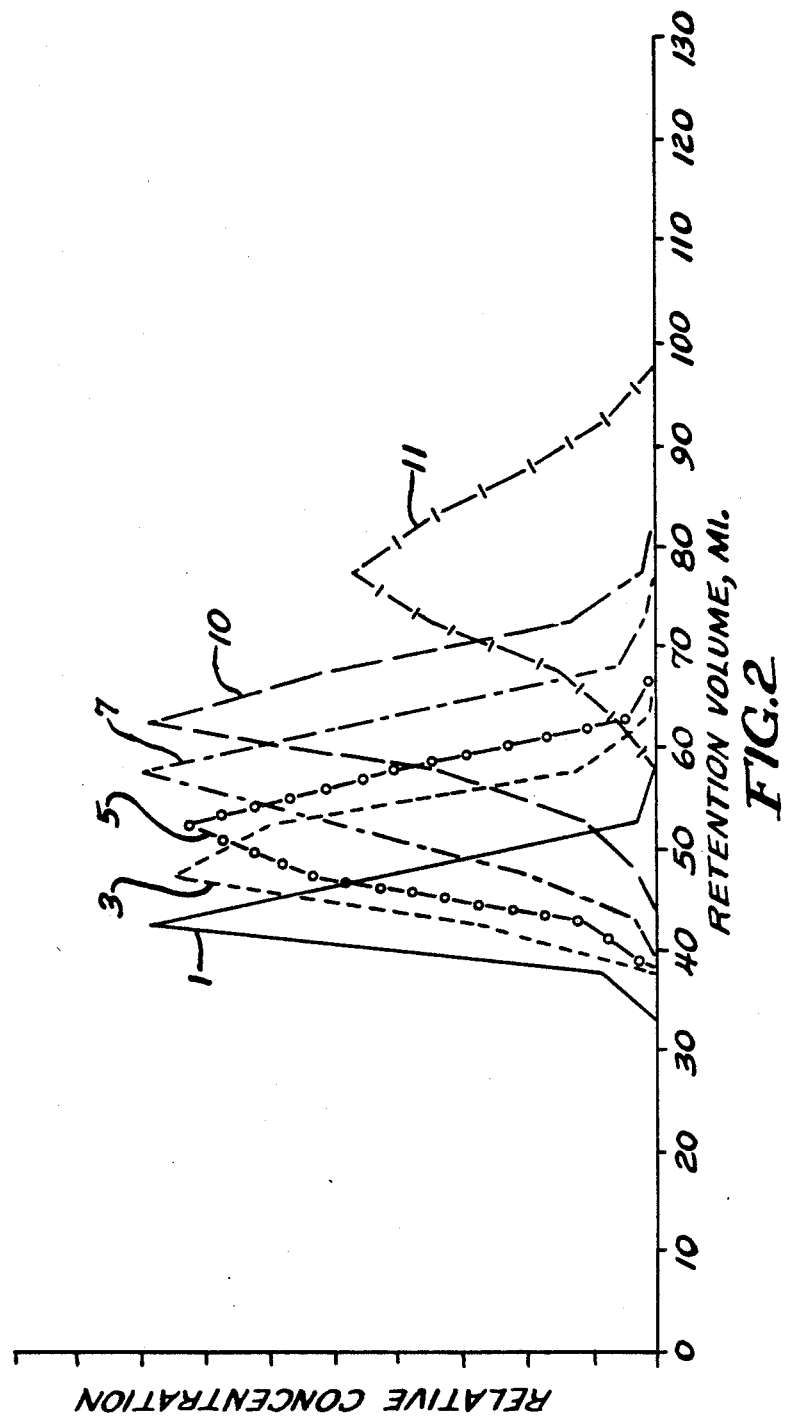
FIG. 2 is similar to FIG. 1 except that the desorbent diluent is n-octane.

Another pulse test was run under the same conditions and with the same materials as Example I, except that the desorbent was diluted with n-octane instead of n-heptane and the tracer was n-$C_6$ instead of n-$C_9$. The feed was 2 cc of a solution containing 0.5 g each of the following materials: n-$C_6$; ethylbenzene, p-xylene, m-xylene, o-xylene and p-ethyltoluene. The adsorbent was dried to yield an LOI of 0.64%. The results are shown in FIG. 2 and the following Table 2.

TABLE 2

| Component | Gross Retention Volume (ml) | Net Retention Volume (ml) | Peak Width At Half Height (ml) | Selectivity $\beta$ |
| --- | --- | --- | --- | --- |
| n-$C_6$ | 43.8 | 0 | 8.3 | Tracer |
| Ethylbenzene | 56.9 | 13.1 | 12.3 | 2.61 |
| p-Xylene | 63.5 | 19.7 | 11 | 1.74 |
| m-Xylene | 49.1 | 5.3 | 11.2 | 6.45 |
| o-Xylene | 51.8 | 8 | 12.6 | 4.28 |
| p-Ethyltoluene | 78 | 34.2 | 16.9 | 1.00 (Ref.) |

EXAMPLE III

Another pulse test was run under the same conditions and with the same materials as Example I, except that the column flow rate was 1.31 cc/min and the desorbent was 1-methyl naphthalene diluted in n-heptane. The results are shown in the following Table 3, indicating good separation between p-ethyltoluene and the next most strongly adsorbed components, cumene and p-xylene.

TABLE 3

| Component | Gross Retention Volume (ml) | Net Retention Volume (ml) | Selectivity $\beta$ |
| --- | --- | --- | --- |
| n-Nonane | 46.4 | 0.0 | Tracer |
| Ethylbenzene | 57.7 | 11.4 | 2.40 |
| p-Xylene | 61.7 | 15.3 | 1.79 |
| m-Xylene | 50.6 | 4.2 | 6.52 |
| o-Xylene | 51.7 | 5.3 | 5.17 |
| Cumene | 61.9 | 15.6 | 1.76 |
| p-Propylbenzene | 53.9 | 7.5 | 3.65 |
| p-Ethyltoluene | 73.8 | 27.4 | 1.0 (Ref.) |
| Mesitylene | 48.4 | 2.0 | 13.7 |
| 1,2,4-Trimethylbenzene | 54.5 | 8.2 | 3.34 |
| 1,2,3-Trimethylbenzene | 51.3 | 4.9 | 5.59 |

EXAMPLE IV

Another pulse test was run under the same conditions and with the same materials as Example I, except that the temperature was 200° C., the flow rate was 1.34 cc/min and the desorbent was a 30/70 wt. % mixture of methyl tetralin and n-heptane. The methyl-tetralin was a 35/65 wt. % mixture of the two isomers, 5-methyl tetralin and 6-methyl tetralin. The LOI of the adsorbent, KY, was 0.01% at 500° C. The results are shown in the following Table 4, indicating adequate separation of p-ethyltoluene from the next most strongly adsorbed component, p-xylene.

TABLE 4

| Component | Gross Retention Volume (ml) | Net Retention Volume (ml) | Selectivity $\beta$ |
|---|---|---|---|
| n-Nonane | 41.3 | 0.0 | Tracer |
| Mesitylene | 46.8 | 5.6 | 5.71 |
| n-Propylbenzene | 48.4 | 7.1 | 4.44 |
| m-Xylene | 49.1 | 7.8 | 4.06 |
| o-Xylene | 52.5 | 11.2 | 2.83 |
| 1,2,3-Trimethylbenzene | 55.7 | 14.4 | 2.21 |
| 1,2,4-Trimethylbenzene | 57.3 | 16.0 | 1.98 |
| Ethylbenzene | 58.3 | 17.1 | 1.85 |
| Cumene | 59.4 | 18.1 | 1.75 |
| p-Xylene | 65.8 | 24.5 | 1.29 |
| p-Ethyltoluene | 73.0 | 31.7 | 1.00 (Ref.) |

What is claimed is:

1. A process for separating p-ethyltoluene from a mixture comprising p-ethyltoluene and at least one other component selected from $C_8$ aromatic hydrocarbons and other $C_9$ aromatic hydrocarbons, which process comprises contacting said mixture with a type Y zeolite adsorbent containing potassium ions at exchangeable cationic sites at adsorption conditions to effect the selective adsorption of said p-ethyltoluene by said adsorbent and to produce a raffinate stream comprising the less strongly adsorbed $C_9$ hydrocarbons and said $C_9$ aromatic hydrocarbons and contacting said adsorbent with a desorbent comprising 1,2,3,4-tetrahydronaphthalene or a lower alkyl derivative thereof or an alkyl derivative of naphthalene at desorption conditions to effect the removal of p-ethyltoluene from said adsorbent as an extract stream.

2. The process of claim 1 wherein said feed mixure comprises at least one $C_9$ aromatic hydrocarbon selected from the group consisting of mesitylene, 1,2,3-trimethylbenzene, 1,2,4-trimethylbenzene and cumene.

3. The process of claim 1 wherein said desorbent is tetralin.

4. The process of claim 1 wherein said desorbent is 1-methyl naphthalene.

5. The process of claim 1 wherein said desorbent is methyl tetralin.

6. The process of claims 2 wherein said raffinate is fractionated to recover said other $C_9$ aromatic hydrocarbons and said $C_8$ aromatic hydrocarbons and said desorbent material and recycling said desorbent material to the desorption step of said process.

* * * * *